(12) United States Patent
Weber (10) Patent No.: US 7,494,497 B2
(45) Date of Patent: Feb. 24, 2009

(54) MEDICAL DEVICES

(75) Inventor: Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 893 days.

(21) Appl. No.: 10/335,604

(22) Filed: Jan. 2, 2003

(65) Prior Publication Data

US 2004/0133223 A1    Jul. 8, 2004

(51) Int. Cl.
*A61B 17/22* (2006.01)
(52) U.S. Cl. ...................................... 606/159
(58) Field of Classification Search .................. 606/159, 606/169, 170, 171, 174, 180
See application file for complete search history.

(56) References Cited

U.S. PATENT DOCUMENTS

| | | | |
|---|---|---|---|
| 5,397,355 A | 3/1995 | Marin et al. | |
| 5,593,417 A | 1/1997 | Rhodes | |
| 5,593,434 A | 1/1997 | Williams | |
| 5,616,149 A | 4/1997 | Barath | |
| 5,713,913 A | 2/1998 | Lary et al. | |
| 5,792,158 A * | 8/1998 | Lary | 606/159 |
| 5,800,526 A | 9/1998 | Anderson et al. | |
| 6,197,013 B1 | 3/2001 | Reed et al. | |
| 6,383,215 B1 | 5/2002 | Sass | |
| 6,632,231 B2 * | 10/2003 | Radisch, Jr. | 606/159 |

* cited by examiner

*Primary Examiner*—Kevin T. Truong
(74) *Attorney, Agent, or Firm*—Crompton, Seager & Tufte, LLC (57) ABSTRACT

Medical devices, such as medical balloons, catheters having balloons, and stents, having one or more cutting elements are disclosed. In some embodiments, the cutting elements include diamond.

20 Claims, 7 Drawing Sheets

MEDICAL DEVICES

TECHNICAL FIELD

The invention relates to medical devices, such as medical balloons, catheters having balloons, and stents.

BACKGROUND

The body includes various passageways such as arteries, other blood vessels, and other body lumens. These passageways sometimes become occluded by a tumor or restricted by plaque. To widen an occluded body vessel, balloon catheters can be used, for example, in angioplasty.

A balloon catheter can include an inflatable and deflatable balloon carried by a long and narrow catheter body. The balloon is initially folded around the catheter body to reduce the radial profile of the balloon catheter for easy insertion into the body.

During use, the folded balloon can be delivered to a target location in the vessel, e.g., a portion occluded by plaque, by threading the balloon catheter over a guide wire emplaced in the vessel. The balloon is then inflated, e.g., by introducing a fluid into the interior of the balloon. Inflating the balloon can radially expand the vessel so that the vessel can permit an increased rate of blood flow. In some cases, it is desirable to incise at least a portion of the plaque, which can further widen the vessel and increase the rate of blood flow. After use, the balloon is deflated and withdrawn from the body.

In another technique, the balloon catheter can also be used to position a medical device, such as a stent or a stent-graft, to open and/or to reinforce a blocked passageway. For example, the stent can be delivered inside the body by a balloon catheter that supports the stent in a compacted or reduced-size form as the stent is transported to the target site. Upon reaching the site, the balloon can be inflated to deform and to fix the expanded stent at a predetermined position in contact with the lumen wall. The balloon can then be deflated, and the catheter withdrawn.

SUMMARY

The invention relates to medical devices, such as medical balloons, catheters having balloons, stents, and stent-grafts. In one aspect, the invention features a medical device including one or more cutting elements, or atherotomes.

In another aspect, the invention features a medical device including an inflatable balloon, a cutting element carried by the balloon, and a deformable member different than the balloon. The member is disposed over a portion of the cutting element.

Embodiments can include one or more of the following features. The cutting element includes diamond. The cutting element includes a material having a hardness of greater than about 5,700 kg/mm$^2$. The cutting element has a cutting edge, and the deformable member, e.g., a polymer, extends over the cutting edge. The polymer can be a silicone rubber or a urethane. The device further includes a second member between the cutting element and the balloon, the second member having a hardness greater than the hardness of the deformable member. The second member can be a polyimide or a polyamide. The medical device does not include the deformable member.

The device can include a plurality of cutting elements carried by the balloon. The plurality of cutting elements can be arranged collinearly and carried by the balloon. The device can include two adjacent cutting elements arranged overlapping relative to a longitudinal direction of the balloon.

The cutting element can have a cutting edge with a radius of curvature less than about 50 nanometers, e.g., less than about 20 nanometers, or less than about 10 nanometers.

The balloon can be smaller than a 10 French balloon, e.g., smaller than a 7 French, 5 French, or 3 French balloon.

In another aspect, the invention features a medical device including an inflatable balloon, and a cutting element carried by the balloon. The cutting element has a hardness greater than about 5,700 kg/mm$^2$. The cutting element can include diamond. The balloon can be smaller than a 10 French balloon, e.g., a 7 French, 5 French, or 3 French balloon.

In another aspect, the invention features a medical device including an inflatable balloon smaller than a 10 French balloon, and a cutting element carried by the balloon. The cutting element can include diamond. The balloon can be smaller than a 10 French balloon, e.g., a 7 French, 5 French, or 3 French balloon.

In another aspect, the invention features a method of using a medical device. The method includes providing the device having an inflatable balloon, a cutting element carried by the balloon, and a deformable member different than the balloon, the member being disposed over the cutting element, and expanding the balloon, the cutting element piercing the deformable member.

The cutting element can have a cutting edge, and the method further includes radially reducing the balloon, the deformable member covering the cutting edge. The cutting element can pierce through the deformable member as the deformable member is contacted against a vessel wall.

In another aspect, the invention features an endoprosthesis including an expandable tubular member, and a cutting element disposed on the tubular member.

Embodiments can include one or more of the following features. The cutting element includes diamond. The cutting element includes a material having a hardness greater than about 5,700 kg/mm$^2$. The cutting element has a cutting edge with a radius of curvature of less than about 50 nanometers. The cutting element has a cutting edge, and the stent further comprises a deformable member extending over the cutting edge. The endoprosthesis further includes a polymeric layer over a portion of the tubular member. The endoprosthesis further includes a drug-releasing layer over a portion of the tubular member. The endoprosthesis includes a plurality of cutting elements disposed on the tubular member. The tubular member is balloon-expandable or self-expandable.

Embodiments may include one or more of the following advantages. The cutting element can be formed relatively sharp, and as a result, can provide well-defined, regular cuts with relatively low forces. Reducing random, uncontrolled cracking can reduce inflammation and/or restenosis of a body vessel. The cutting element can be formed relatively thin and flexible, e.g., without compromising strength. As a result, the cutting element can be supported by relatively small medical devices, such as catheters and stents, that are capable of being delivered through tortuous and narrow body lumens. The cutting element is biocompatible. The cutting element is compatible with magnetic resonance imaging (MRI). Endoprostheses having cutting elements can provide the cutting action of a cutting balloon and the expansion of an endoprosthesis in one step, which can be convenient and save time.

Other features and advantages of the invention will be apparent from the description of the preferred embodiments thereof and from the claims.

DETAILED DESCRIPTION

Figure 1:
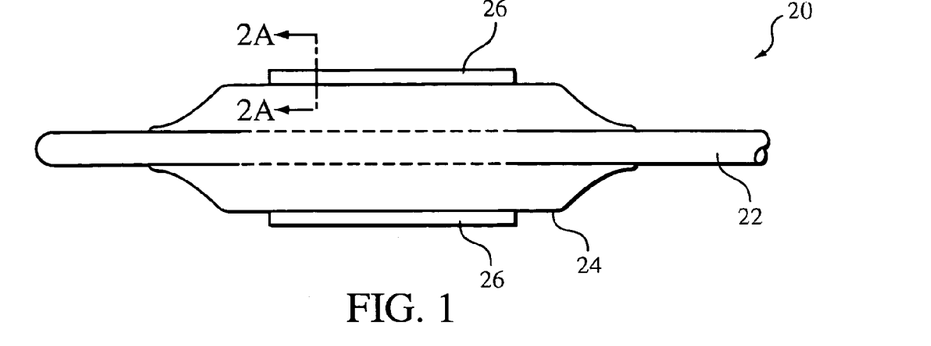
FIG. 1 is an illustration of an embodiment of a medical device.
Figure 2A:
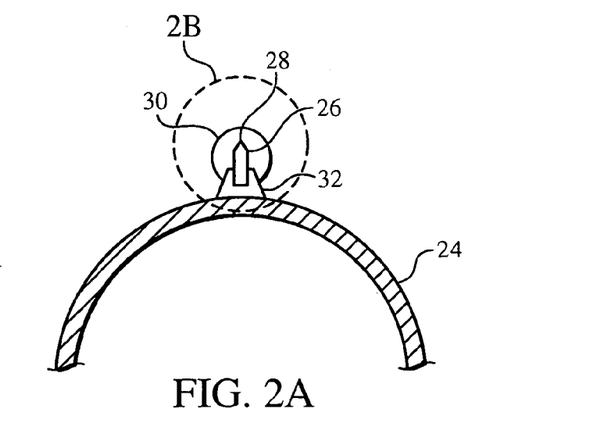
FIG. 2A is a cross sectional view of the medical device of FIG. 1, taken along line 2-2.
Figure 2B:
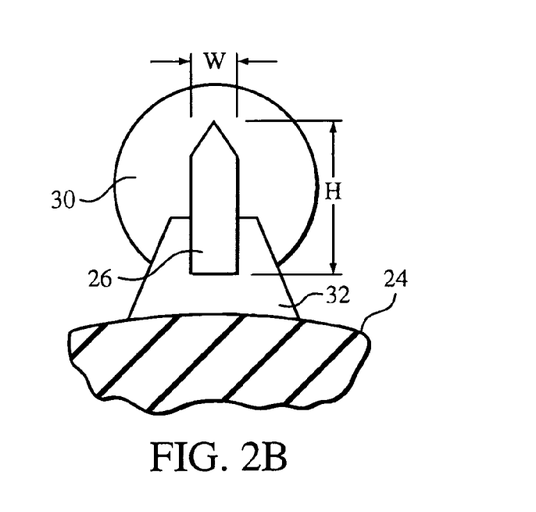
FIG. 2B is a detailed view of a portion of FIG. 2A.

Referring to FIG. 1, a balloon catheter 20 includes a catheter body 22, an inflatable balloon 24 attached to the catheter body, and one or more cutting elements 26, or atherotomes, (here, two) carried by the balloon. Referring to FIGS. 2A and 2B, cutting element 26 is supported by a base 32 (e.g., by an adhesive) that is secured to balloon 24, for example, by an adhesive such as a urethane. Cutting element 26 includes a cutting edge 28, which is covered by a resilient material 30. Resilient material 30 can protect balloon 24 from the cutting edge and/or protect a vessel wall from the cutting edge, e.g., during insertion and withdrawal of catheter 20. During use, described in detail below, cutting edge 28 can pierce through resilient material 30, thereby allowing cutting element 26 to cut, for example, plaque or a calcified material that is occluding a body vessel.

Cutting elements 26 are elongated members (e.g., blades) preferably formed of diamond. Because of its physical properties, diamond enhances cutting element 26 by allowing cutting edge 28 to be formed with relatively high sharpness. A sharp cutting edge typically lowers the forces needed for cutting. Lower cutting forces can provide a relatively controlled, precise cut with enhanced regularity and less distortion, thereby reducing the occurrence of damage to the vessel wall. Sharpness can be measured as a radius of curvature of cutting edge 28, e.g., using scanning electron microscopy (SEM). In embodiments, cutting edge 28 has a radius of curvature less than about 50 nanometers. The radius of curvature can be equal to or less than about 50, 40, 30, 20, 10, 5, or 3 nanometers; and/or equal to or greater than about 3, 5, 10, 20, 30, or 40 nanometers. In embodiments of catheter 20 having multiple cutting elements 26, two or more of the cutting elements can have the same or different sharpness. Different sharpness can provide different degrees of cutting.

A cutting element formed of diamond can also be relatively hard, and have a small friction coefficient and a small thermal expansion coefficient. In embodiments, cutting element 26 has a hardness of greater than or equal to about 4,000 kg/mm$^2$, e.g., between about 5,700-19,400 kg/mm$^2$ (Knoops hardness at 298K), and/or an elongation modulus of greater than or equal to about 1,140 GPa. The enhanced hardness allows cutting element 26 to be formed relatively thin, e.g., without compromising strength. As a result, cutting element 26 can be relatively flexible. Enhanced flexibility allows cutting element 26 to travel well through tortuous paths of a body vessel or passageway. In embodiments, cutting element 26 has a width (W, FIG. 2B) less than or equal to about 0.006 inch, e.g., less than or equal to about 0.005 inch, 0.004 inch, 0.003 inch, 0.002 inch, or 0.001 inch. The length of cutting element 26 can be about 1-30 mm, e.g., about 5-20 mm, or about 10-15 mm. The height (H, FIG. 2B) of cutting element 26 can be less than or equal to about 0.013 inch, e.g., less than or equal to about 0.011 inch, 0.009 inch, 0.007 inch, or 0.005 inch. The dimensions of cutting element 26 typically are a function of the size of balloon catheter 20 that carries the cutting element (s). In embodiments of catheter 20 having multiple cutting elements 26, two or more of the cutting elements can have the same or different dimensions. Different dimensions can provide different degrees of cutting and/or flexibility.

In some embodiments, only a portion of cutting element 26 is formed of diamond. For example, a diamond member defining a cutting edge can be attached (e.g., glued) to a support, such as a metal (e.g., steel or Nitinol), ceramic, or polymer support, carried by the balloon. A support, such as a Nitinol or polymer support, can be flexible, which can enhance the flexibility of the balloon. The diamond member can be made relatively small, e.g., smaller relative to the dimensions described above. One or more of the total dimensions of the diamond member and the support can be generally as described above.

Furthermore, since cutting element 26 can be formed relatively thin, while still providing effective cutting, a relatively small balloon catheter can be used to carry the cutting element. In embodiments, balloon catheter 20 is a 10 French device or smaller. For example, balloon catheter 20 can be equal to smaller than a 9 French, 8 French, 7 French, 6 French (2.00 mm O.D.), 5 French, 4 French, 3 French, 2 French, or 1 French (1.00 mm O.D.) device. As a result, catheter 20 can be delivered to relatively narrow target sites, such as coronary arteries (e.g., those having a diameter less than about 2 mm), cranial arteries, and peripheral arteries (e.g., those in the lower extremities).

Diamond cutting elements 26 are commercially available from GFD Gesellschaft für Diamantprodukte mbH (Ulm, Germany), which uses a plasma polishing process. Methods of making diamond cutting tools are described in U.S. Pat. No. 4,989,578, and methods of polishing diamond is described in U.S. Pat. No. 6,284,315.

Resilient material 30 can be made of any material that can deform upon compression. It is also desirable that the material can elastically recover to an undeformed state when the compression is removed. Resilient material 30 can be made of a polymer, such as a rubber (e.g., a silicone rubber) or a soft polyurethane (e.g., Tecothane 55D). Resilient material 30 can be covered with a coating, such as a hydrophilic coating, to reduce friction. Examples of suitable materials include a hydrogel layer having a hydrophilic polymeric material such as (alkoxy) polyalkylene glycol, a copolymer of methylvinyl ether and maleic acid, poly(vinylpyrrolidone) (PVP), poly(N-alkylacrylamide), poly(acrylic acid), poly(vinyl alcohol), poly(ethyleneimine), polyamide, (carboxy)methyl cellulose, polyvinyl sulfonic acid, heparin, dextran, modified dextran and chondroitin sulfate, polyethylene oxide, poly(vinyl pyrrolidone), or a PVP/vinyl acetate copolymer. Resilient material 30 can be attached base 32 using an adhesive or by heat bonding.

Base 32 can be any material that is compatible, e.g., can be bonded with, balloon 24, cutting element 26, the adhesive, and/or resilient member 30. The material for base 32 can be relatively hard to provide a rigid support for cutting element 26, particularly during cutting, and to spread the cutting force from the cutting element to a larger area on balloon 24. In some cases, base 32 can be formed of a metal (such as stainless steel, tantalum, tungsten, Nitinol, titanium, or niobium) anchored or molded to balloon 24, or a polymer (such as a polyimide or a polyamide, e.g., Nylon 12). Certain materials for base 32 are MRI compatible, such as Nitinol, titanium, or niobium. Base 32 can be generally triangular, as shown, or non-triangular, e.g., rectangular, rhomboid, or trapezoid.

Examples of balloon catheter 20 are described in, for example, Wang U.S. Pat. No. 5,195,969, and Hamlin U.S. Pat. No. 5,270,086, both hereby incorporated by reference; and are exemplified by the Express® or Maverick® systems available from Boston Scientific Scimed, Maple Grove, Minn. In some cases, balloon 24 is a non-elastic balloon, e.g., a nondistendable balloon made of, e.g., PET. Balloon 24 can include one or more biaxially-oriented layers.

Figure 3A:
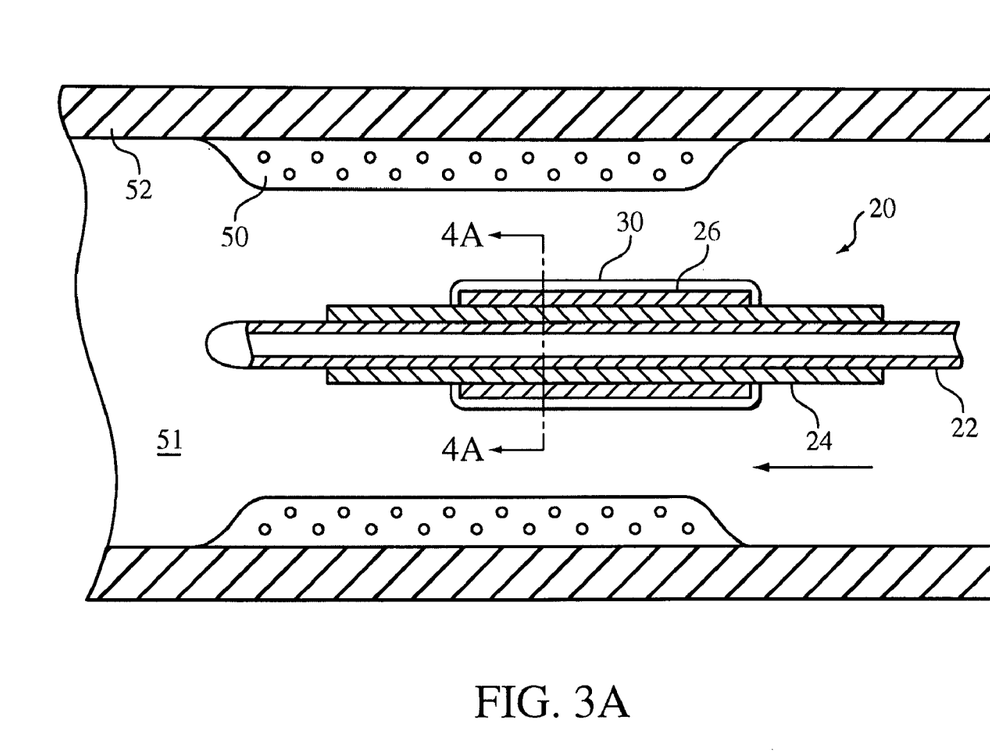
FIGS. 3A, 3B, and 3C illustrate an embodiment of a method of using the medical device of FIG. 1.
Figure 3B:
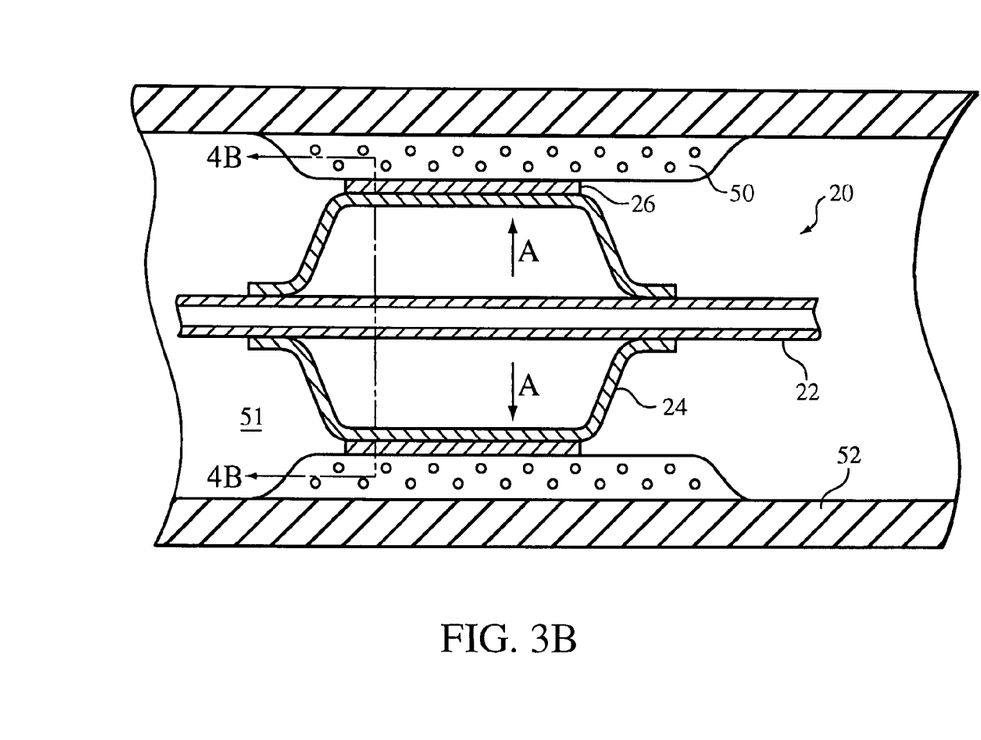
Figure 3C:
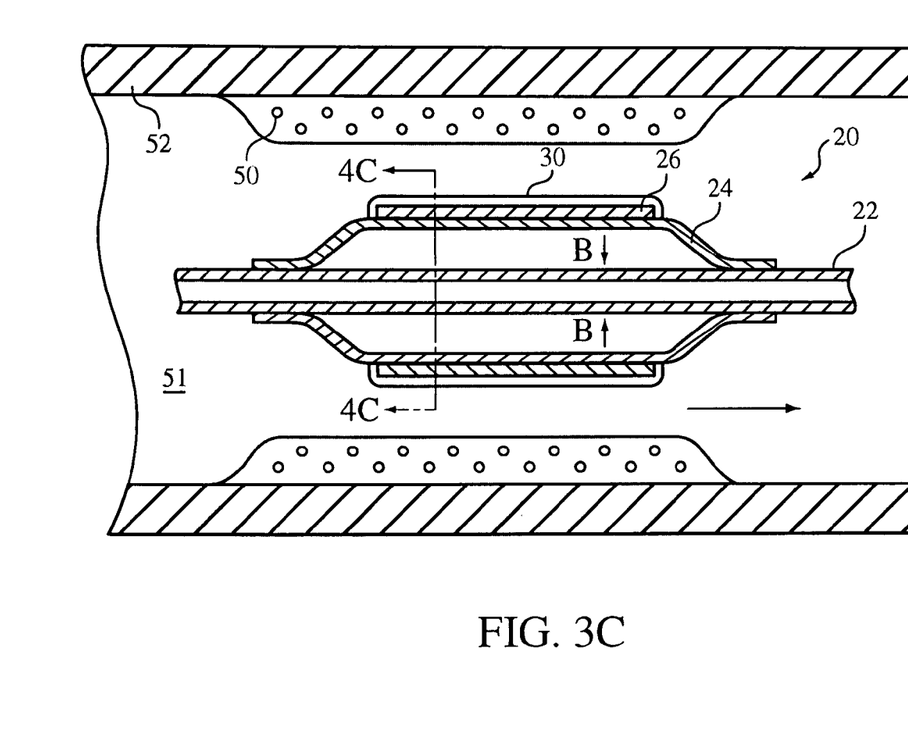
Figure 4A:
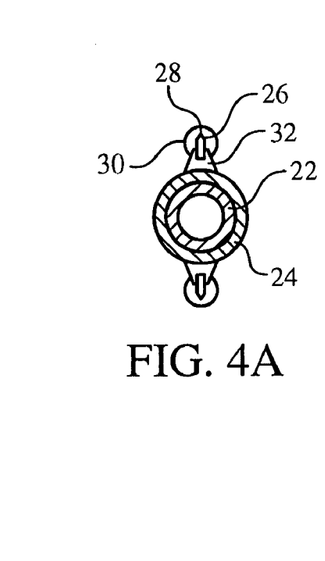
FIGS. 4A, 4B, and 4C are cross sectional views of the medical device shown in FIGS. 3A, 3B, and 3C, respectively, taken along lines 3A-3A, 3B-3B, and 3C-3C, respectively.
Figure 4B:
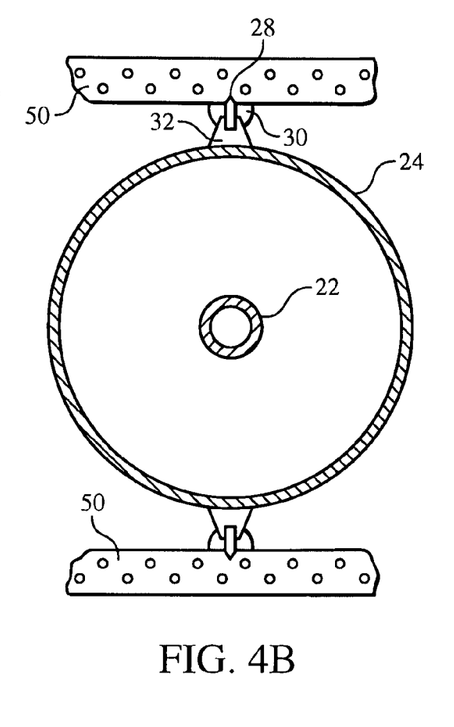
Figure 4C:
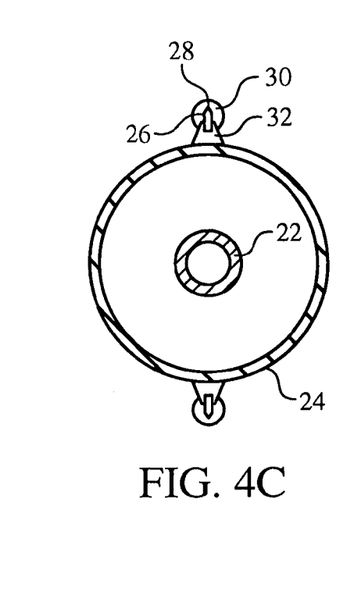

Referring to FIGS. 3A, 3B, and 3C, a method of using catheter 20 is shown. Catheter 20 is delivered to a target site 51, e.g., one having a calcified region 50, using conventional methods, such as by threading catheter body 22 over an emplaced guide wire (not shown) (FIG. 3A). Balloon 24 is unexpanded, and cutting edge 28 is covered by resilient material 30 to prevent the cutting edge from contacting vessel wall 52 (FIG. 4A). After catheter 20 is properly positioned, balloon 24 is radially expanded (arrows A), e.g., by introducing a fluid into the interior of the balloon via an inflation lumen (not shown) extending along catheter body 22. As balloon 24 is expanded, resilient material 30 and cutting element 26 are advanced radially toward calcified region 50. As balloon 24 if expanded further, resilient material 30 contacts calcified region 50 and compresses against the calcified region. With further expansion and compression, resilient material 30 deforms (e.g., compresses and bulges), and cutting edge 28 pierces through the resilient member, thereby cutting calcified region 50 (FIG. 4B). Catheter 20 can be moved (e.g., translated and/or rotated) to provide a desired cutting action. Subsequently, balloon 24 is radially reduced, thereby withdrawing cutting elements 26 away from calcified region 50. As a result, the compressive forces against resilient material 30 are removed. The resilient material elastically recovers to its undeformed state in which the material covers cutting edge 28. Catheter 20 can be removed according to conventional methods.

OTHER EMBODIMENTS

In some embodiments, a drug or therapeutic agent, e.g., heparin, is placed or encapsulated between resilient material 30 and cutting element 26. The drug or agent is released into a cutting area as edge 28 penetrates through resilient material 30 during use. Examples of drugs and therapeutic agents are disclosed in U.S. Pat. No. 5,674,242; U.S. Ser. No. 09/895,415, filed Jul. 2, 2001; and U.S. Ser. No. 10/232,265, filed Aug. 30, 2002. The therapeutic agents or pharmaceutically active compounds can include, for example, anti-thrombogenic agents, antioxidants, anti-inflammatory agents, anesthetic agents, anti-coagulants, and antibiotics.

In other embodiments, a sponge coating can be placed on balloon 24 or an endoprosthesis (described below). The sponge coating, e.g., a non-hydrogel polymer having voids, can be loaded with a drug, e.g., heparin, to release the drug during expansion of the balloon or endoprosthesis. Examples of sponge coatings, including methods of making them, and suitable drugs, are described in U.S. Pat. No. 6,364,856.

While catheter 20 is shown having two cutting elements 26, in other embodiments, the catheter can have one, three, four, five, six, seven, eight, or more cutting elements. Cutting elements 26 can be equally and/or unequally spaced around the circumference of balloon 24. For example, looking at a radial cross section (e.g., FIG. 4A) of a balloon having six cutting elements 26, the cutting elements can be formed at 2 o'clock, 3 o'clock, 4 o'clock, 8 o'clock, 9 o'clock, and 10 o'clock. Cutting element 26 at 3 o'clock is equally spaced from the cutting elements at 3 o'clock and 4 o'clock; but, for example, the cutting element at 4 o'clock is unequally spaced from the cutting elements at 3 o'clock and 8 o'clock. Cutting elements 26 can be symmetrically or asymmetrically positioned around the circumference of balloon 24.

Figure 5:
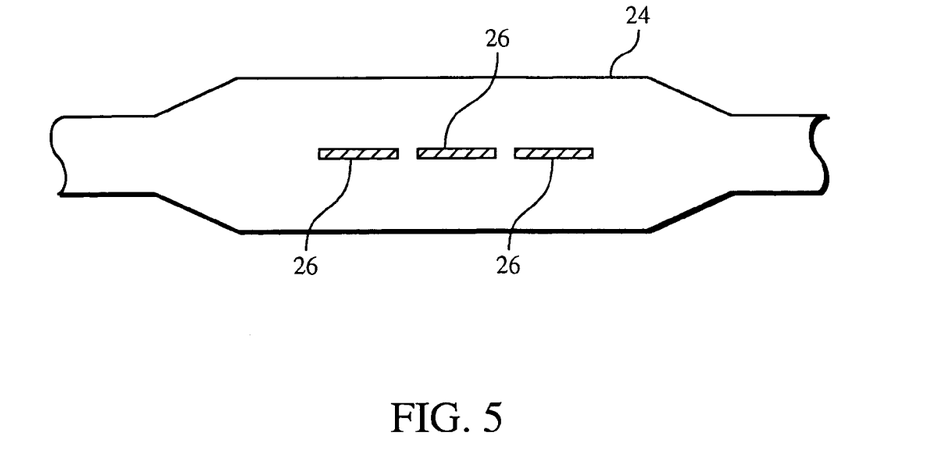
FIG. 5 is a schematic plan view of an embodiment of a medical device.
Figure 6:
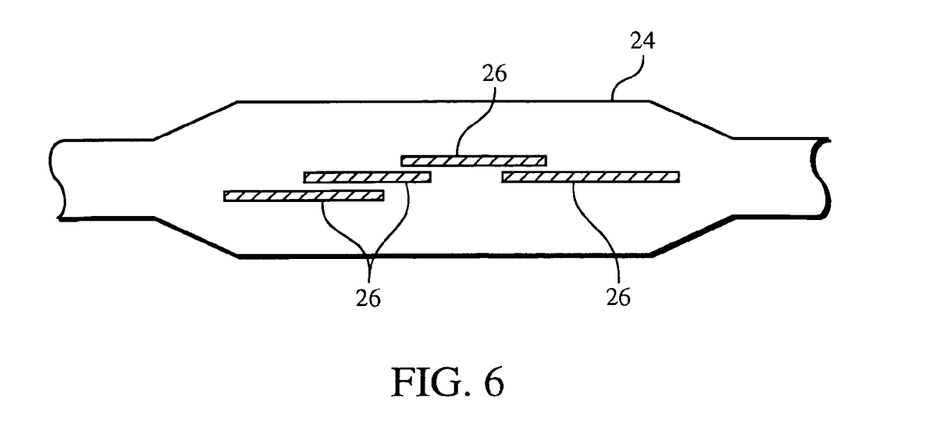
FIG. 6 is a schematic plan view of an embodiment of a medical device.

Multiple cutting elements 26, e.g., two, three, four, five, six, or more, can be arranged collinearly (e.g., spaced and end-to-end) along balloon 24 (FIG. 5), which can enhance the flexibility of the balloon. Multiple cutting elements 26 can be arranged side-by-side, e.g., adjacent to each other. Multiple cutting elements 26 can be arranged adjacent to each other and overlapping along the longitudinal direction of balloon 24 (FIG. 6). A balloon can have one or more sets of cutting elements arranged as described above.

Other methods of attaching cutting elements 26 to balloon 24 are possible. Cutting elements 26 can be thermally and/or mechanically bonded. For example, cutting elements 26 can include projections, e.g., hooks, at their base that embed into the wall of balloon 24. The projections can be embedded manually. The cutting elements can be appropriately positioned in the balloon-forming mold with the projections extending into the cavity of the mold. The projections are embedded into the wall of the balloon as a parison or a tube is radially expanded (e.g., blow molded) to form the balloon. Cutting element 26 may include one or more openings through which the material of base 32 can extend, thereby further securing the cutting element to the base. Cutting element(s) 26 can be attached directly to balloon 24, e.g., without base 32. For example, cutting element can be elongated blades having a triangular cross section in which the base is attached to the balloon and the cutting edge is formed at the apex of the triangular section (FIG. 5).

Figure 7:
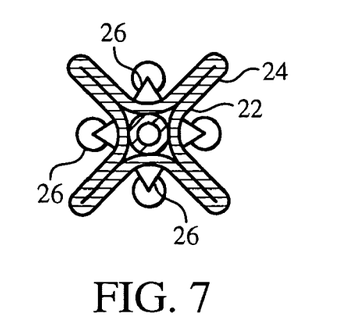
FIG. 7 is a cross sectional view of an embodiment of a medical device.
Figure 8:
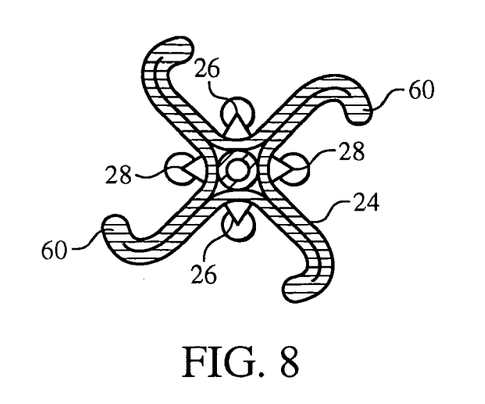
FIG. 8 is a cross sectional view of an embodiment of a medical device.

Alternatively or in addition to resilient material 30, balloon 24 can be folded (FIG. 7) using the methods described in Vigil U.S. Pat. Nos. 5,209,799 and 5,336,234, both hereby incorporated by reference, to protect cutting elements 26. In some cases, referring to FIG. 8, relatively compliant areas of balloon 24, e.g., flaps 60, can be folded over cutting elements 26 to further protect the body lumen from cutting edges 28. Folding can be performed by engaging, e.g., grasping, flaps 60 with a chuck, and rotating the chuck. Folding can be performed during heat treatment of balloon 24, as described in Vigil U.S. Pat. No. 5,209,799. Other methods of folding balloon 24 are described in U.S. Ser. No. 10/087,303.

In other embodiments, balloon 24 and/or catheter body 22 can have a wall having a plurality of layers formed of polymers. Multilayer devices are described in Hamlin U.S. Pat. No. 5,270,086; Wang U.S. Pat. No. 5,195,969; Hamilton U.S. Pat. No. 5,797,877; and U.S. Ser. No. 09/798,749, entitled "Multilayer Medical Device" and filed on Mar. 2, 2001, all hereby incorporated by reference in their entirety. The layers can be selected to provide catheter body 22 and/or balloon 24 with desired properties. Different combinations of layering, e.g., materials, sequence, and/or thickness, can be used, as described in U.S. Ser. No. 09/798,749.

Figure 9:
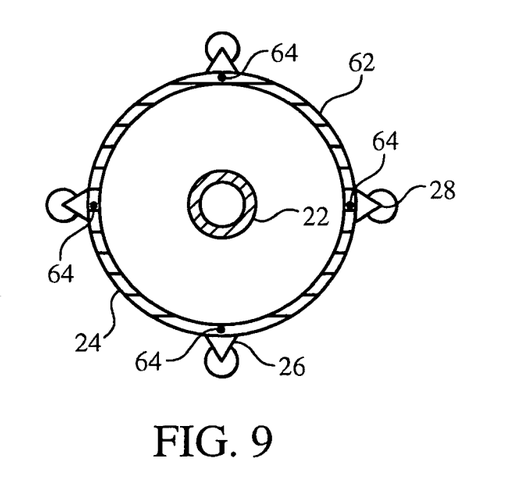
FIG. 9 is a cross sectional view of an embodiment of a medical device.

Referring to FIG. 9, in embodiments, balloon 24 can be co-extruded to include a matrix material 62 and discrete (e.g., individually distinct) striped portions 64 (here, four) surrounded by the matrix material. Cutting elements 26 are attached to balloon 24 over striped portions 64. In embodiments, striped portions 64 are formed of a material(s) having a lower compliancy than material(s) that are not in the striped portions, such as those of matrix material 62. Alternatively or in addition, striped portions 64 are formed of a material(s) having a lower distensibility than material(s) that are not in the striped portions. Compliancy and distensibility may apply to the radial direction and/or the longitudinal direction of balloon 24. Alternatively or in addition, striped portions 64 are stiffer, harder, and/or stronger than non-striped portions of balloon 24.

Attaching cutting elements 26 over striped portions 64 enhances the attachment between the cutting elements and balloon 24. For example, as balloon 24 is inflated (e.g., up to 10 atm or higher) and deflated during use, striped portions 64 are less likely to change, e.g., grow or distend, longitudinally and/or radially, relative to non-striped portions of the balloon, such as compliant portions made of the matrix material. The interface between cutting elements 26 and striped portions 64 can remain relatively constant during use. As a result, mechanical stress between cutting elements 26 and balloon 24 reduced, and attachment therebetween is enhanced.

Striped portions 64 can also enhance folding and refolding of balloon 24. A striped portion 64 and areas adjacent to the striped portions can behave like a hinge. For example, a (relatively non-compliant) striped portion 62 can act as a stationary member of a hinge and the (relatively compliant) adjacent areas can act as moveable members of the hinge that pivot about the interfacial region between the striped portion and the adjacent areas. When balloon 24 is deflated, it can fold along the interfacial region so that compliant areas form flaps, and striped portions 64 are positioned in furrows. As a result, balloon 24 can be formed and used with a relatively low profile and a relatively predictable folding configuration, thereby providing desirable insertion and withdrawal of catheter 20 from a subject. Embodiments of balloon 24 and stripes portions 64 are described in U.S. Ser. No. 10/083,926, entitled "Medical Device" and filed on Feb. 27, 2002, hereby incorporated by reference. Cutting element(s) 26 can be attached directly to the balloon or indirectly, e.g., through base 32.

Figure 10:
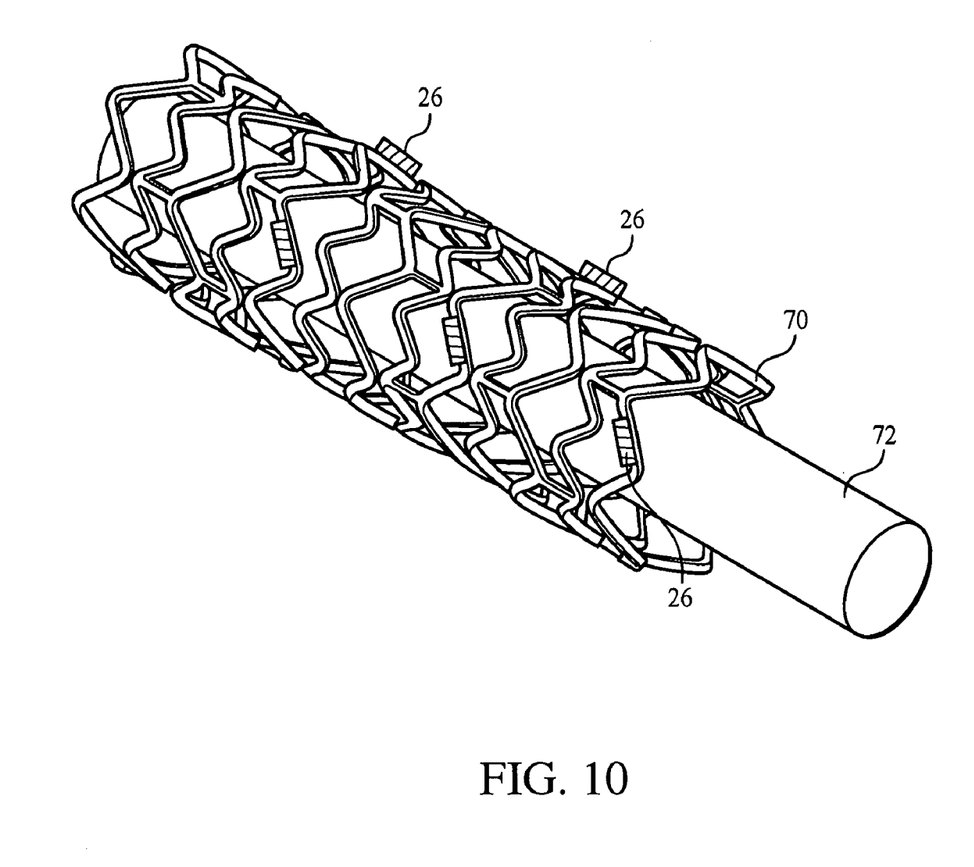
FIG. 10 is a perspective view of an embodiment of a medical device.

Referring to FIG. 10, in other embodiments, one or more cutting elements 26 can be carried by an endoprosthesis 70, such as a stent or a stent-graft, here shown on a support such as a balloon catheter or a catheter shaft 72. As shown, cutting elements 26 are mounted on the struts of endoprosthesis 70. During expansion, cutting elements 26 can cut a calcified region, which can reduce the amount of force used to expand endoprosthesis. Cutting elements 26 can be mounted on endoprosthesis 70 using a biocompatible adhesive or cement, such as DiamondLink™ (available from Biodent, Quebec, Canada).

Embodiments of the cutting elements on endoprosthesis 70 can be the same as those described above, and can be arranged on the endoprosthesis the same as those on balloon 24. Alternatively or in addition to resilient material 30, the cutting elements on endoprosthesis 70 can be sprayed with a polymer, such as styrene-isobutylene-styrene (SIBS, a tri-blocked polymer) to protect the cutting edges, e.g., during delivery and/or crimping. In other embodiments, a drug or therapeutic agent (e.g., placitaxel or those described above) can be placed between cutting elements 26 and resilient member 30 or the polymer. The drug can be released to a cutting site as endoprosthesis 70 is expanded and cutting elements 26 penetrate the site.

To crimp endoprosthesis 70, a soft polymer tube, e.g., one thicker than the cutting elements, can be placed inside the cavity of a crimper or around the endoprosthesis. The tube can distribute the crimping force over a broad area of endoprosthesis 70, thereby reducing damage to the cutting elements. Alternatively or in addition, the polymer, e.g., SIBS, can be applied to the cutting elements after crimping. The polymer can be applied to cutting elements 26 on balloon 24. Methods of crimping endoprostheses and devices for crimping are described, for example, in Austin, U.S. Pat. No. 6,360,577, hereby incorporated by reference. Other suitable systems are described in U.S. Ser. No. 10/087,303. Crimping devices are also commercially available, e.g., from Machine Solutions Inc. (Flagstaff, Ariz.).

In general, the endoprostheses can be of any desired shape and size (e.g., coronary stents, aortic stents, peripheral stents, gastrointestinal stents, urology stents and neurology stents). In certain embodiments, a coronary stent can have an expanded diameter of from about 2 millimeters to about 6 millimeters. In some embodiments, a peripheral stent can have an expanded diameter of from about 5 millimeters to about 24 millimeters. In certain embodiments, a gastrointestinal and/or urology stent can have an expanded diameter of from about 6 millimeters to about 30 millimeters. In some embodiments, a neurology stent can have an expanded diameter of from about 1 millimeter to about 12 millimeters. The endoprostheses can be balloon-expandable, self-expandable, or a combination of both (e.g., U.S. Pat. No. 5,366,504).

In other embodiments, the endoprosthesis can include and/or be attached to a biocompatible, non-porous or semi-porous polymer matrix made of polytetrafluoroethylene (PTFE), expanded PTFE, polyethylene, urethane, or polypropylene. The endoprosthesis can include a releasable therapeutic agent or a pharmaceutically active compound, such as described in U.S. Pat. No. 5,674,242, and commonly assigned U.S. Ser. No. 09/895,415, filed Jul. 2, 2001. The therapeutic agents or pharmaceutically active compounds can include, for example, anti-thrombogenic agents, antioxidants, anti-inflammatory agents, anesthetic agents, anti-coagulants, and antibiotics.

The endoprosthesis can be used, e.g., delivered and expanded, according to conventional methods. Suitable catheter systems are described in, for example, Wang U.S. Pat. No. 5,195,969, and Hamlin U.S. Pat. No. 5,270,086. Suitable stents and stent delivery are also exemplified by the NIR on Ranger® system, available from Boston Scientific Scimed, Maple Grove, Minn. Other methods of carrying and delivering an endoprosthesis is described in U.S. Ser. No. 10/283,815, filed Oct. 30, 2002, and entitled "Medical Devices With Magnetic Powered Actuation".

The medical devices described above can include radiopaque markers and/or markers that are visible by magnetic resonance imaging (MRI)) portions or markers to help the user position the devices. For example, a portion of cutting element 26 can be coated with a radiopaque and/or MRI visible material; balloon 24 may include one or more marker bands;

and the wire of the stent or stent-graft can be radiopaque and/or MRI visible. Suitable radiopaque materials include, for example, gold, platinum, tungsten, tantalum, and metal alloys containing a sufficient percentage of heavy elements. Suitable MRI visible materials include, for example, non-ferrous metal-alloys containing paramagnetic elements (e.g., dysprosium or gadolinium) such as terbium-dysprosium, dysprosium, terbium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni).

All publications, references, applications, and patents referenced in this application are herein incorporated by reference in their entirety.

Other embodiments are within the claims.

What is claimed is:

1. A medical device, comprising:
   an inflatable balloon;
   a cutting element carried by the balloon; and
   a deformable member disposed to extend over at least a portion of the cutting element;
   wherein the cutting element comprises a material having a hardness of greater than about 5,700 $kg/mm^2$, Knoops hardness, and wherein the cutting element, upon expansion of the inflatable balloon, pierces through the deformable member.

2. The device of claim 1, wherein the cutting element comprises diamond.

3. The device of claim 1, wherein the cutting element has a cutting edge, and the deformable member extends over the cutting edge.

4. The device of claim 3, wherein the deformable member comprises a polymer.

5. The device of claim 4, wherein the polymer is a material selected from a group consisting of a silicone rubber and a urethane.

6. The device of claim 1, further comprising a second member between the cutting element and the balloon, the second member having a hardness greater than the hardness of the deformable member.

7. The device of claim 6, wherein the second member comprises a material selected from a group consisting of a polyimide and a polyamide.

8. The device of claim 1, comprising a plurality of cutting elements carried by the balloon.

9. The device of claim 1, comprising a plurality of cutting elements arranged collinearly and carried by the balloon.

10. The device of claim 1, comprising two adjacent cutting elements arranged overlapping relative to a longitudinal direction of the balloon.

11. The device of claim 1, wherein the cutting element has a cutting edge with a radius of curvature less than about 50 nanometers.

12. The device of claim 1, wherein the cutting element has a cutting edge with a radius of curvature less than about 20 nanometers.

13. The device of claim 1, wherein the cutting element has a cutting edge with a radius of curvature less than about 10 nanometers.

14. The device of claim 1, wherein the balloon is smaller than a 10 French balloon.

15. The device of claim 1, wherein the balloon is smaller than a 7 French balloon.

16. The device of claim 1, wherein the balloon is smaller than a 5 French balloon.

17. The device of claim 1, wherein the balloon is smaller than a 3 French balloon.

18. A method of using a medical device, the method comprising:
    providing the device having an inflatable balloon, a cutting element carried by the balloon, and a deformable member disposed over a portion of the cutting element wherein the cutting element comprises a material having a hardness of greater than about 5,700 $kg/mm^2$, Knoops hardness; and
    expanding the balloon, the cutting element piercing through the deformable member.

19. The method of claim 18, wherein the cutting element has a cutting edge, and further comprising radially reducing the balloon, the deformable member covering the cutting edge.

20. The method of claim 18, wherein the cutting element pierces through the deformable member as the deformable member is contacted against a vessel wall.

* * * * *